(12) United States Patent
Kokkelink et al.

(10) Patent No.: US 9,414,748 B2
(45) Date of Patent: Aug. 16, 2016

(54) TOMOGRAPHY PROBE

(75) Inventors: Jan W. Kokkelink, Blairstown, NJ (US); Talal K. Findakly, Hackettstown, NJ (US)

(73) Assignee: Micro-Optics, Inc., Hackettstown, NJ (US)

(*) Notice: Subject to any disclaimer, the term of this patent is extended or adjusted under 35 U.S.C. 154(b) by 2531 days.

(21) Appl. No.: 11/705,616

(22) Filed: Feb. 13, 2007

(65) Prior Publication Data

US 2008/0194947 A1 Aug. 14, 2008

(51) Int. Cl.
*A61B 8/14* (2006.01)
*A61B 5/00* (2006.01)

(52) U.S. Cl.
CPC ............ *A61B 5/0073* (2013.01); *A61B 5/0066* (2013.01); *A61B 5/0088* (2013.01)

(58) Field of Classification Search
CPC .......... A61B 17/2251; A61B 17/2256; A61B 17/2258; A61B 5/6844; A61B 5/6886; A61B 8/4281; A61N 7/02
USPC ................................................ 600/476–478
See application file for complete search history.

(56) References Cited

U.S. PATENT DOCUMENTS

| | | | |
|---|---|---|---|
| 6,252,666 B1 | 6/2001 | Mandella et al. | 356/479 |
| 6,501,551 B1 | 12/2002 | Tearney et al. | 356/477 |
| 6,564,089 B2 | 5/2003 | Izatt et al. | 600/478 |
| 2003/0086093 A1 | 5/2003 | Bush | 356/479 |

OTHER PUBLICATIONS

Transmittal Letter to the Commissioner for Patents dated Dec. 19, 2006; Utility Patent Application Transmittal Form; Fee Transmittal Form for FY2006;specification of Nonprovisional Utility Patent with Claims; Drawings of Utility Patent; executed Oath or Declaration for Utility or Design Patnet Application; Declaration of Additional Inventors; and Non-Publication Request Under 35 U.S.C. 122(b)(2)(B)(i), all filed by Optiphase, Inc.

*Primary Examiner* — Mark Remaly
(74) *Attorney, Agent, or Firm* — Michael W. Ferell

(57) ABSTRACT

An optical probe suitable for medical or dental tomography is switchable between a rotating and non-rotating mode to control interference between source signals and data signals. The probe is suitably constructed in an in-line configuration and uses Faraday rotators which rotate polarization in the same direction in a rotating mode and rotate polarization in opposite directions in a non-rotating mode.

27 Claims, 3 Drawing Sheets

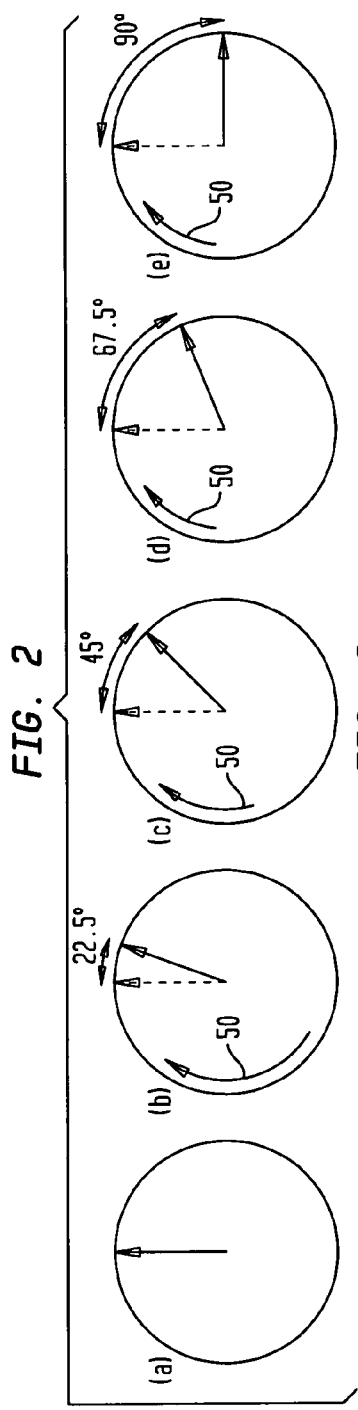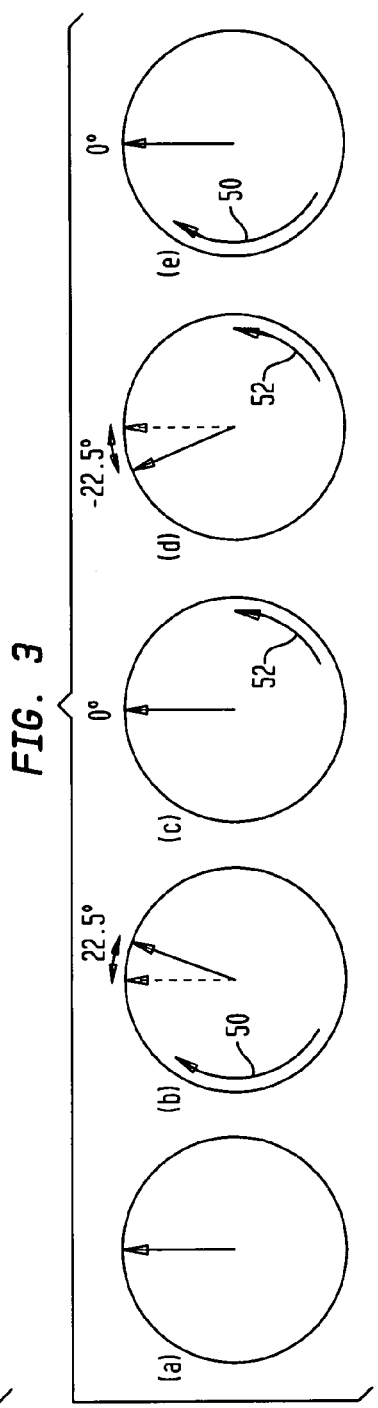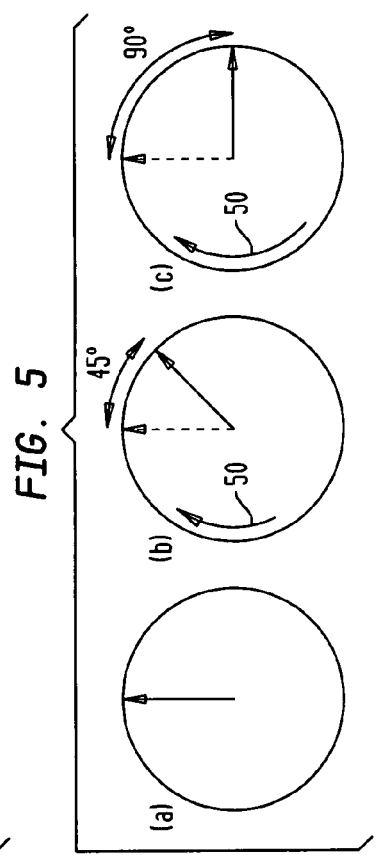

TOMOGRAPHY PROBE

TECHNICAL FIELD

The present invention relates to optical tomography and more specifically to an optical probe having an in-line construction and preferably using a pair of Faraday rotators switchable between a rotating mode and a non-rotating mode.

BACKGROUND

Optical tomography for medical and dental applications is known in the art. In U.S. Pat. No. 6,564,089 of Izatt et al. entitled "Optical Imaging Device" there is disclosed an Optical Coherence Tomography (OCT) device which irradiates a biological tissue with low coherence light, obtains a high resolution tomogram of the inside of the tissue by low-coherent interference with scattered light from the tissue, and is provided with an optical probe which includes an optical fiber having a flexible and thin insertion part for introducing the low coherence light. When the optical probe is inserted into a blood vessel or a patient's body cavity, the OCT enables the doctor to observe a high resolution tomogram. The OCT is provided with polarization compensation means such as a Faraday rotator on the side of the light emission of the optical probe, so that the OCT can obtain the stabilized interference output regardless of the state of the bend. See, also, U.S. Pat. No. 6,252,666 of Mandella et al. entitled "Method and Apparatus for Performing Optical Coherence-Domain Reflectometry and Imaging Through a Scattering Medium Employing a Power-Efficient Interferometer".

In U.S. Pat. No. 6,501,551 to Tearney et al. entitled "Fiber Optic Imaging Endoscope Interferometer With at Least One Faraday Rotator" there is disclosed an imaging system for performing optical coherence tomography which includes an optical radiation source; a reference optical reflector; a first optical path leading to the reference optical reflector; and a second optical path coupled to an endoscopic unit. The endoscopic unit preferably includes an elongated housing defining a bore; a rotatable single mode optical fiber having a proximal end and a distal end positioned within and extending the length of the bore of the elongated housing; and an optical system coupled to the distal end of the rotatable single mode optical fiber. The system further includes a beam divider dividing the optical radiation from the optical radiation source along the first optical path to the reflector and along the second optical path; and a detector positioned to receive reflected optical radiation from the reflector transmitted along the first optical path and reflected optical radiation transmitted from the structure along the second optical path. The detector generates a signal in response to the reflected optical radiation from the reference reflector and the reflected optical radiation from the structure. A processor generates an image of the structure in response to the signal from the detector.

In United States Patent Application Publication No. US 2003/0086093 to Bush entitled "All Fiber Autocorrelator" there is disclosed an autocorrelator apparatus and method for measuring physical properties of an object where the measurement path is at least semi-translucent to light. The apparatus includes a non-coherent light fiber interferometer and an optional coherent light fiber interferometer in association so as to share PZT fiber modulators.

Despite advances in the art, tomography probes and associated equipment tend to be expensive and difficult to fabricate, often requiring polarization maintaining ("PM") components. Moreover, many systems require beam-splitters and the like which makes compact fabrication difficult, if not impossible, such that tomography probes are often much bulkier than desired.

SUMMARY OF INVENTION

There is provided in one aspect of the invention an in-line optical tomography probe of compact dimensions suitable for medical or dental tomography.

In another aspect of the invention, there is provided an optical tomography probe which has a pair of Faraday rotators which are operated in either a rotating (additive) mode or a non-rotating (canceling) mode in order to control interference with the source signal.

A preferred construction of the probe includes an optical fiber suitable for connecting the probe to an optical signal source and an optical data analyzer; at least a first lens disposed in-line with the optical fiber; as well as a reference reflector disposed in-line with the optical fiber and the first lens. The optical fiber is adapted for providing an optical source signal to the first lens and receiving an optical reference signal as well as receiving reflected optical data signals which are derived from the optical source signal and reflected from a target. The first lens is adapted to focus the reference signal and reflected optical data signals into the optical fiber and adapted for collimating the optical source signal along an axis of the probe. The reference reflector is adapted to generate the reference signal from the optical source signal by reflecting a portion of the optical source signal. There is further provided a first Faraday rotator disposed in-line with the optical fiber, the first lens, the reference reflector; the first Faraday rotator being operative to rotate the polarization state of traversing optical signals in a first direction of rotation by about 22.5° in a single pass. Also provided is a second Faraday rotator disposed in-line with the optical fiber, the first lens, the reference reflector and the first Faraday rotator; the second Faraday rotator being operative to rotate the polarization state of traversing optical signals by about +22.5° in a single pass with respect to the first direction of rotation in a rotating mode and being operative in a non-rotating mode to rotate the polarization of traversing optical signals by about −22.5° with respect to the first direction of rotation; whereby the optical probe is configured to provide the optical fiber with the optical reference signal generated from the optical source signal as well as provide an optical data signal which has been reflected from the target and has a polarization state which has been rotated about 90° by the Faraday rotators in the rotating mode or an optical data signal which has been reflected from the target and has a polarization state which has been rotated about 0° by the Faraday rotators in the non-rotating mode. Optical interference between the optical reference signal and the optical data signals which have been reflected from the target is controlled by selection of the rotating mode or the non-rotating mode of the probe. The source signal exits the probe through a probe signal input/output lens to the target while optical data signals which have been reflected from the target are collected through the probe input/output lens.

Further aspects and advantages of the present invention will become apparent from the discussion which follows.

BRIEF DESCRIPTION OF DRAWINGS

The invention is described in detail below with reference to the drawings, wherein like numerals designate similar parts and wherein:

FIGS. 2(a)-2(e) are schematic representations illustrating operation of the tomography probe of FIG. 1 in the rotating mode;

FIGS. 3(a)-3(e) are schematic representations illustrating operation of the probe of FIG. 1 in the non-rotating mode.

FIG. 5 is a schematic representation illustrating operation of the tomography probe of FIG. 4 in the rotating mode.

DETAILED DESCRIPTION

The invention is described in detail below for purposes of illustration only. Modifications within the spirit and scope of the present invention, set forth in the appended claims, will be readily apparent to those of skill in the art.

As used herein, terminology has its ordinary meaning, for example, mm means millimeter, nm means nanometer and so forth as the context indicates.

"Faraday rotator" refers an optical device that rotates the polarization of light due to the Faraday effect, which in turn is based on a magneto-optic effect. The Faraday rotator works because one polarization of the input light is in ferromagnetic resonance with the material which causes its phase velocity to be higher than the other. The plane of linearly polarized light is rotated when a magnetic field is applied parallel to the propagation direction. The empirical angle of rotation is given by:

$$\beta = vBd$$

where $\beta$ is the angle of rotation (in radians). B is the magnetic flux density in the direction of propagation (in teslas). d is the length of the path (in metres) where the light and magnetic field interact. Then $v$ is the Verdet constant for the material. This empirical proportionality constant (in units of radians per tesla per metre, rad/(T·m)) varies with wavelength and temperature and is known for various materials.

"Maximum cross-section span" refers to the maximum thickness of the body of the probe housing the Faraday rotator (s) and the lenses. For a cylindrical probe, the maximum cross-section span is simply the diameter of the probe at its central portion.

"Polarization state" refers to the relative polarization angle of optical signals provided to and from the probe. The polarization of the optical signals may be elliptical, circular or linear.

"Single mode" refers to the number of the modes allowed in a given fiber determined by a relationship between the wavelength of the light passing through the fiber, the core diameter of the fiber, and the material of the fiber. This relationship is known as the Normalized Frequency Parameter, or V number. The mathematical description of the V number is:

$$V = 2*(\pi)*NA*a/\lambda$$

where:
NA=Numerical Aperture (see below)
a=fiber radius (microns)
$\lambda$=wavelength (microns)

A single-mode fiber has a V number that is less than 2.405, for most optical wavelengths. It will propagate light in a single guided mode. A multi-mode fiber has a V number that is greater than 2.405, for most optical wavelength and therefore will propagate in many paths through the fiber.

Figure 1:
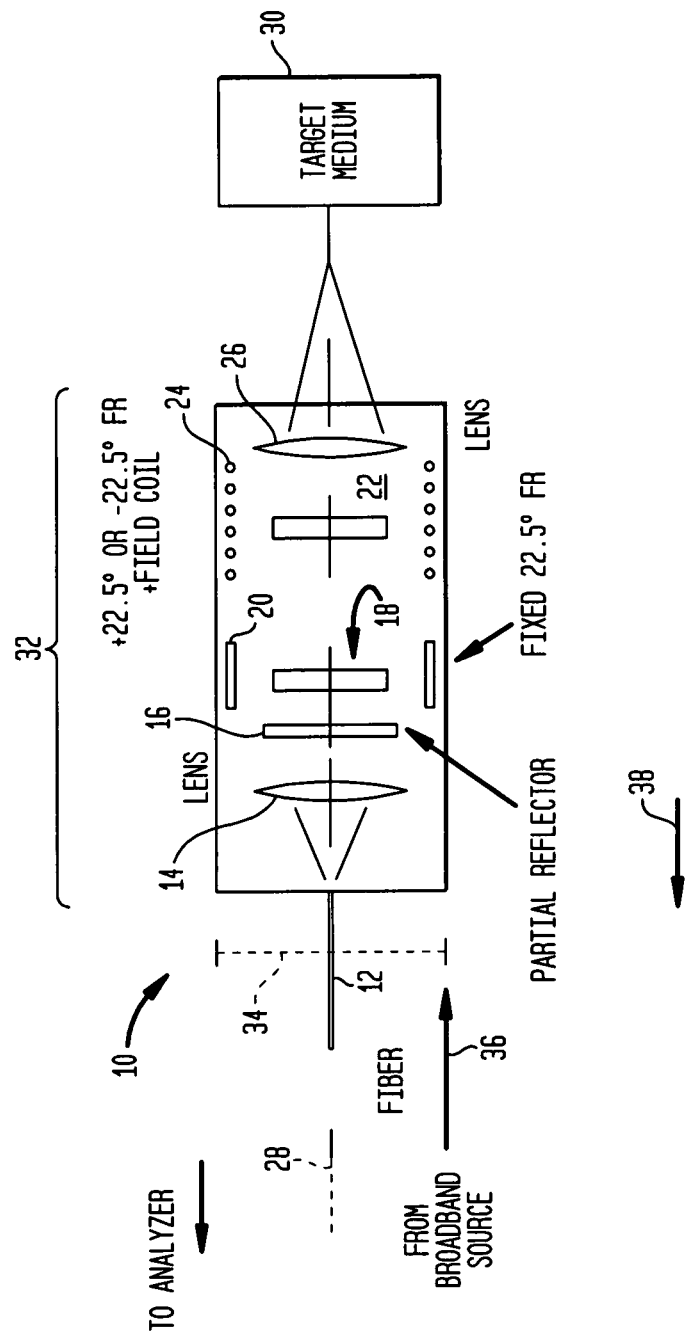
FIG. 1 is a schematic diagram of a first optical tomography probe configured in accordance with the present invention.

There is shown schematically in FIG. 1 an in-line optical probe 10 constructed in accordance with the present invention. Probe 10 includes a single mode optical fiber 12, as well as a first lens 14 disposed in-line with the single mode input/output fiber. There is further provided a reference reflector 16 also disposed in-line with single mode fiber 12 and the first lens 14.

The single mode input/output fiber is adapted for receiving an optical input signal from a broadband source, for example, which is supplied to optical fiber 12. The broadband source may be a 1300 nm source with a bandwidth of about 15 nm or so as is well known. Fiber 12 is likewise operable as a single mode waveguide for a traversing optical data signal which is derived from the input signal and has been reflected from a target. Lens 14 is adapted to focus the reference signal and a traversing optical data signal into the signal mode fiber and reflector 16 is a partial reflector adapted to generate a reference signal from the optical input signal supplied to the probe as will be further discussed herein.

Also provided as part of the probe is a first Faraday rotator 18 provided with a fixed magnet 20 and a second Faraday rotator 22 provided with a field coil 24. A second lens 26 also acts as an input/output for the probe. Faraday rotator 18, Faraday rotator 22 and lens 26 are likewise disposed, in-line with optical fiber 12, lens 14, and reflector 16.

Figure 4:
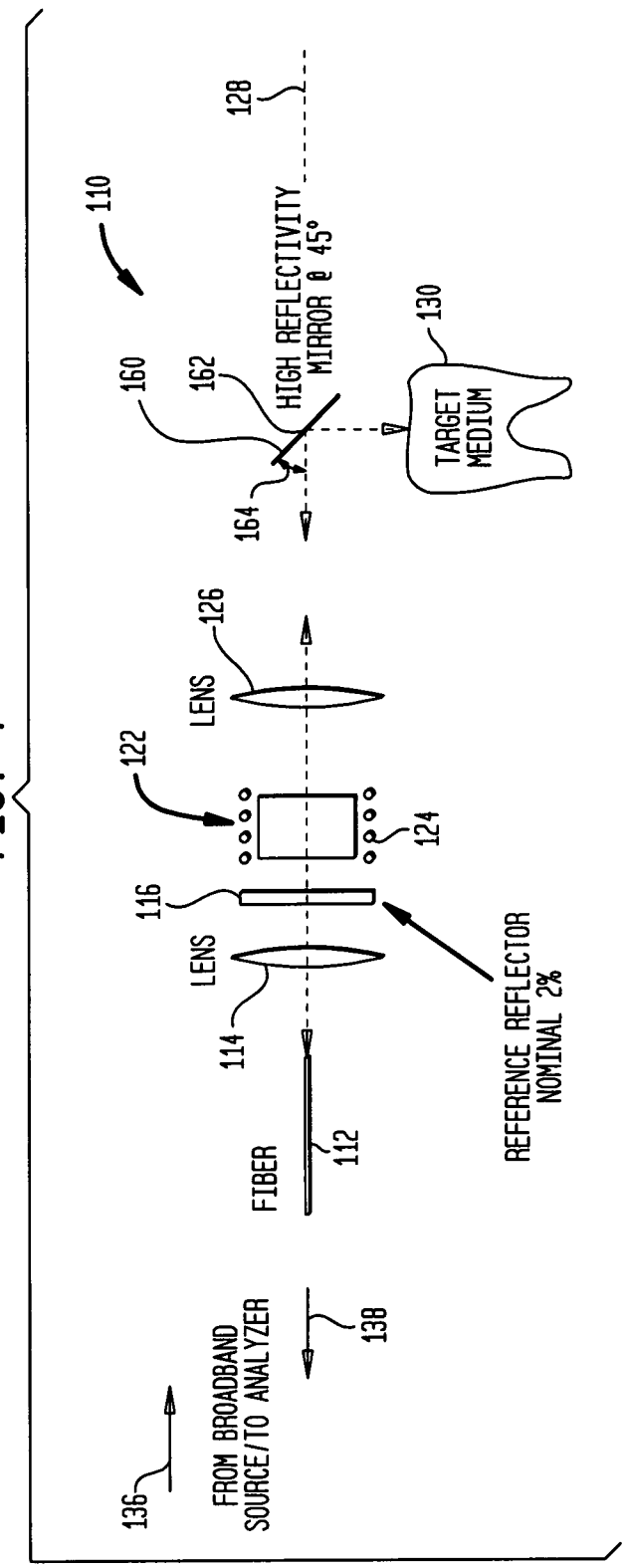
FIG. 4 is a schematic diagram showing a second optical tomography probe configured in accordance with the present invention and its operation in a dental application.

By in-line, we refer to the fact that all of the various components including the axis (and end) of fiber 12 are aligned along axis 28 (128) of probe 10 (110) as is shown generally in FIGS. 1 and 4.

The Faraday rotators are selected, configured and arranged such that they are switchable between a rotating mode where the Faraday rotators are operative to rotate a polarization state of a traversing optical signal by about 90° and a non-rotating mode where the polarization state of the traversing optical data signal is rotated by about 0° as signals traverse the probe in both directions as described hereinafter, this ensures that the data signal will interfere with the reference signal regardless of the polarization rotation imparted by the target. The optical fiber is adapted for providing an optical source signal to the first lens and receiving an optical reference signal as well as receiving reflected optical data signals which are derived from the optical source signal and reflected from a target.

The first lens is adapted to focus the reference signal and reflected optical data signals into the optical fiber and adapted for collimating the optical source signal along an axis of the probe; and the reference reflector is adapted to generate the reference signal from the optical source signal by reflecting a portion of the optical source signal. The optical probe is thus configured to provide the optical fiber with the optical reference signal generated from the optical source signal as well as provide an optical data signal which has been reflected from the target and has a polarization state which has been rotated about 90° by the Faraday rotators in a rotating mode or an optical data signal which has been reflected from the target and has a polarization state which has been rotated about 0° by the Faraday rotators in a non-rotating mode.

The various components shown schematically in FIG. 1 are readily available and the probe is easily assembled since a PM structure is not required. Any suitable type of Faraday rotator may be employed, for example, "A" type rotators available from Mitsubishi Gas Chemical Co. (MGC) of the bismuth, iron, garnet (BIG) type; or other types which require external magnetic fields such as yttrium, iron, garnet (YIG) rotators may be used.

The various elements are arranged as shown about along longitudinal axis 28 of the probe, preferably such that a central portion 32 where lens 14, reflector 16, Faraday rotator 18 and Faraday rotator 22 are mounted has a maximum cross-section span 34 of less than 30 mm. Suitably, the cross-section span is the diameter for cylindrical probes and is less than 20 mm in many cases. A maximum cross-section span of from about 5-10 mm is desirable in some cases.

In order to gather tomographic information from a target such as target 30 in FIG. 1 or dental, a signal source is provided from a broadband source, for example, to input/output fiber 12 and provided it to the probe in direction 36. The broadband source signal provided in direction 36 has a characteristic polarization state may be linear, may be circular, or may be elliptical. For present purposes, we refer to the source signal as having a relative polarization of 0° as shown in FIG. 2(a), and describe operation without rotation of the reflected signal by the target; for illustrative purposes, only.

FIGS. 2(a)-2(e) illustrate schematically the relative polarization state rotation of the source signal and reflected data signals as they traverse probe 10 when the probe is in a rotating mode, while FIGS. 3(a)-3(e) illustrate schematically the relative polarization state rotation of the source signal and the reflected data signals when probe 10 is operated in a non-rotating mode. The construction shown in FIG. 1 is particularly advantageous when Faraday rotator is selected from commonly available YIG rotators, BIG rotators or the like, since most of these rotators will scatter light when a magnetic field is absent.

A source signal having the relative polarization state shown schematically in FIG. 2(a) is provided to lens 14, which collimates the signal and provides it to partial reflector 16. At reflector 16 a reference output signal is generated and reflected in an output direction 38 as shown on FIG. 1. The reference signal is used for purposes of analyzing the optical signals reflected from the target. Suitable signal analysis equipment is disclosed in U.S. Pat. No. 6,564,089 to Izatt et al. and U.S. patent application Ser. No. 09/992,941 of Bush (Publication No. 2003/0086093), the disclosures of which are incorporated herein by reference.

The source signal travels from partial reflector 16 to the first Faraday rotator 18 which is selected such that the polarization state of the input signal is rotated 22.5° (in a single pass), as the signal proceeds in direction 36. The input signal next encounters Faraday rotator 22 where the signal is rotated an additional 22.5°, that is, plus 22.5° with respect to the direction in which the polarization of the signal has already been rotated. Alternatively, second Faraday rotator 22 may be operated such that the input signal is rotated −22.5° by the rotator in a single pass.

After encountering Faraday rotator 22 the input optical signal is collected by second lens 26 and focused on target 30. At target 30, the input signal is reflected and is referred to as a data signal, or a traversing optical data signal. The reflected signal may have its polarization state partially rotated upon reflection from the target, but for present purposes, we illustrate generally operation of the probe as if such rotation has not occurred.

From the target, the optical data signal is collected by lens 26 and collimated such that it travels in direction 38 along the probe. At rotator 22, coil 24 is operated such that the polarization state of the data signal may be rotated −22.5° or +22.5° relative to the degree of rotation of the input signal by Faraday rotator 18. Thereafter, the output or data signal continues to travel in direction 38 where it encounters Faraday rotator 18. At Faraday rotator 18, the polarization state of the data signal is rotated another 22.5° by the rotator as it traverses Faraday rotator 18. The output signal continues through partial reflector 16 and is focused by lens 14 into signal mode optical fiber 12. Fiber 12 provides the data signals, as well as the reference signal to an analyzer.

The invention is further understood by reference to FIGS. 2(a)-2(e) which illustrate schematically the operation of probe 10 in a rotating mode. The source signal from fiber 12 traveling in direction 36 passes through partial reflector 16 where it still has a relative rotation of 0° as shown in FIG. 2(a). After the signal passes through rotator 18 it is rotated 22.5° in a first direction 50 by the rotator as is shown in FIG. 2(b). The source signal continues in direction 36 to rotator 22 where the signal is rotated another 22.5° in direction 50 by the rotator such that the signal has a relative rotation of its polarization state by 45° with respect to the inputted source signal after it leaves rotator 22 see FIG. 2(c). The source signal is focused by lens 26 to a target 30 where a reflected data signal is generated from the source signal and reflected in direction 38, toward optical fiber 12. The reflected data signal (unrotated by the target in this case) is captured by lens 26, which thus operates as the probe signal input/output and provided to rotator 22. At rotator 22, the polarization state is rotated another 22.5° in direction 50 by rotator 22 such that the data signal has a relative rotation of its polarization state of 67.5° in direction 50 relative to the original input source signal as shown in FIG. 2(d). The data signal then proceeds to rotator 18 where the data signal is rotated another 22.5° such that the polarization state of the reflected signal has been rotated 90° by the probe with respect to the original source signal from which it was derived. The relative polarization state of the data signal provided to lens 14 and fiber 12, 90° is shown schematically in FIG. 2(e).

In order to switch the probe to a non-rotating mode, the current to coil 24 of rotator 22 is reversed such that the coil operates to rotate the polarization state of light in an opposite direction 52 with respect to direction 50. Operation of probe 10 in a polarization non-rotating mode is shown schematically in FIGS. 3(a)-3(e).

A source signal having an arbitrary polarization state shown schematically in FIG. 3(a) is provided to fiber 12 and collimated to partial reflector 16 and Faraday rotators 18, 22. At rotator 18, the source signal is rotated 22.5° in direction 50 by rotator 18 as shown in FIG. 3(b). At rotator 22, the signal is rotated 22.5° in direction 52 such that it has a net rotation of 0° as shown in FIG. 3(c). The signal then exits the probe and is returned as a reflected data signal, which in the case illustrated has not been rotated by the target. At 22, the reflected signal is rotated 22.5° such that it has a net imparted rotation of −22.5° relative to the original signal as is shown in FIG. 3(d). After rotator 22, the reflected data signal is passed to rotator 18 where it is rotated in direction 50 another 22.5° such that when the reflected signal is returned to fiber 12 it has a net imparted rotation of 0° with respect to the source signal from the broadband source. As one of skill in the art will appreciate, the ability to rotate the data signals by about 90° or by about 0° allows one to control interference with the reference signal.

Referring to FIG. 4, there is shown another embodiment of the present invention. In FIG. 4, a probe 110 includes an optical fiber 112, a first lens 114, a partial reflector 116, a Faraday rotator 122 provided with a field coil 124 and an input/output lens 126. The various components are arranged in-line along a longitudinal axis 128. There is additionally provided a mirror 160 movably mounted about an axis at 162 which is substantially orthogonal to axis 128 of probe 110. Preferably, the mirror is movable over an angle 164 which may be varied from 0° to about 80° or at least from about 35° to about 55° to facilitate scanning of the target surface. To this end, the position of mirror 160 may be modulated electronically if so desired in order to scan the target surface.

Probe 110 operates similarly to probe 10 of FIG. 1, except that rotator 122 is selected and operated to rotate the polarization state of a traversing optical signal by 45° when it passes through the rotator in a polarization rotating mode and not to rotate a traversing signal at all in a polarization non-rotating mode.

Referring to FIGS. 4 and 5, probe 110 operates as follows in a polarization rotating mode. A source signal is provided from a broadband source to fiber 112 and travels in a direction 136 in fiber 112. Lens 114 collimates the signal to partial reflector 116 and the source signal is then provided to rotator 122 having the relative polarization state shown in FIG. 5(a). At 122, the source signal is rotated 45° in direction 50 such that it has the relative polarization state shown in FIG. 5(b). The signal continues in direction 136 and exits through lens 126 which focuses the source signal toward mirror 160 which reflects the signal to a target medium such as a tooth 130. The source signal is reflected from the target and returned to mirror 160 as a data signal. The signal reflects from the mirror and is collected by lens 126 and collimated back to rotator 122 where the data signal is rotated another 45° in direction 50 such that it has a relative rotation imparted by rotator 122 of 90° in direction 50 as is shown in FIG. 5(c). The data signal then passes through reflector 116 and is focused into fiber 112 by lens 114 as shown in the diagram.

Probe 110 operates similarly in a non-rotating mode, except that the current provided to coil 124 of rotator 122 is turned off or adjusted such that Faraday rotator 122 does not rotate the polarization state of a traversing optical signal at all.

While the invention has been described in detail, modifications within the spirit and scope of the invention will be readily apparent to those of skill in the art. In view of the foregoing discussion, relevant knowledge in the art and references including co-pending application discussed above in connection with the Background and Detailed Description, the disclosures of which are all incorporated herein by reference, further description is deemed unnecessary.

What is claimed is:

1. An in-line optical probe suitable for medical or dental tomography comprising:
   (a) an optical fiber suitable for connecting the probe to an optical signal source and an optical data analyzer;
   (b) at least a first lens disposed in-line with the optical fiber;
   (c) a reference reflector disposed in-line with the optical fiber and the first lens;
   wherein:
      (i) the optical fiber is adapted for providing an optical source signal to the first lens and receiving an optical reference signal as well as receiving reflected optical data signals which are derived from the optical source signal and reflected from a target;
      (ii) the first lens is adapted to focus the reference signal and reflected optical data signals into the optical fiber and adapted for collimating the optical source signal along an axis of the probe; and
      (iii) the reference reflector is adapted to generate the reference signal from the optical source signal by reflecting a portion of the optical source signal;
   (d) one or more Faraday rotators disposed in-line with the optical fiber, the reference reflector and the first lens;
   wherein the one or more Faraday rotators are selected, configured and arranged such that they are switchable between a rotating mode where the one or more Faraday rotators are operative to rotate a polarization state of optical signals by about 90° and a non-rotating mode where the polarization state of optical signals is rotated by about 0° as signals traverse the probe in both directions;
   whereby the optical probe is configured to provide the optical fiber with the optical reference signal generated from the optical source signal as well as provide (i) an optical data signal which has been reflected from the target and has a polarization state which has been rotated about 90° by one or more Faraday rotators in the rotating mode and (ii) an optical data signal which has been reflected from the target and has a polarization state which has been rotated about 0° by one or more Faraday rotators in the non-rotating mode such that optical interference between the optical reference signal and the optical data signals which have been reflected from the target is controlled by selection of the rotating mode or the non-rotating mode of the probe; and
   (e) a probe signal input/output for providing the source optical signal to the target and collecting optical data signals which have been reflected from the target.

2. The in-line optical probe according to claim 1, wherein the optical fiber is a single mode fiber.

3. The in-line optical probe according to claim 1, wherein the one or more Faraday rotators are switchable between the rotating mode and the non-rotating mode by application of a magnetic field.

4. The in-line probe according to claim 1, further comprising a second lens disposed in-line with the single mode fiber, the first lens, the reference reflector and the Faraday rotators.

5. The in-line optical probe according to claim 4, wherein the second lens is adapted to focus the optical source signal and to capture an optical data signal which has been reflected from the target.

6. The in-line optical probe according to claim 5, wherein the one or more Faraday rotators are disposed between the first and second lenses.

7. The in-line optical probe according to claim 6, further comprising a probe mirror disposed in-line with the optical fiber, the first lens, the reference reflector and the one or more Faraday rotators, the mirror being located outwardly with respect to the second lens and being movably mounted with respect to a mirror axis of the probe.

8. The in-line optical probe according to claim 7, wherein the probe mirror is movably mounted with respect to a longitudinal axis of the in-line optical probe about an axis of rotation generally orthogonal to an axis of the probe.

9. The in-line optical probe according to claim 8, wherein the probe mirror is movably mounted with respect to the axis of the in-line optical probe and movable between an angle of from about 0° to about 80° with respect to the longitudinal axis of the probe.

10. The in-line optical probe according to claim 8, wherein the probe mirror is movably mounted with respect to the axis of the in-line optical probe and movable between an angle of from about 35° to about 55° with respect to the longitudinal axis of the probe.

11. The in-line optical probe according to claim 1, wherein the probe has a maximum cross-section span of 30 mm.

12. The in-line optical probe according to claim 11, wherein the probe has a maximum cross-section span of 20 mm.

13. The in-line optical probe according to claim 12, wherein the probe has a maximum cross-section span of 5-10 mm.

14. An in-line optical probe suitable for medical or dental tomography comprising:
   (a) an optical fiber suitable for connecting the probe to an optical signal source and an optical data analyzer;

(b) at least a first lens disposed in-line with the optical fiber;
(c) a reference reflector disposed in-line with the optical fiber and the first lens;
wherein:
(i) the optical fiber is adapted for providing an optical source signal to the first lens and receiving an optical reference signal as well as receiving reflected optical data signals which are derived from the optical source signal and reflected from a target;
(ii) the first lens is adapted to focus the reference signal and reflected optical data signals into the optical fiber and for collimating the optical source signal along an axis of the probe; and
(iii) the reference reflector is adapted to generate the reference signal from the optical source signal by reflecting a portion of the optical source signal;
(d) a first Faraday rotator disposed in-line with the optical fiber, the first lens, the reference reflector, the first Faraday rotator being operative to rotate the polarization state of traversing optical signals in a first direction of rotation by about 22.5° in a single pass;
(e) a second Faraday rotator disposed in-line with the optical fiber, the first lens, the reference reflector and the first Faraday rotator, the second Faraday rotator being operative to rotate the polarization state of traversing optical signals by about +22.5° in a single pass with respect to the first direction of rotation in a rotating mode and being further operative in a non-rotating mode to rotate the polarization of traversing optical signals by about −22.5° in a single pass with respect to the first direction of rotation;
whereby the optical probe is configured to provide the optical fiber with the optical reference signal generated from the optical source signal as well as provide (i) an optical data signal which has been reflected from the target and has a polarization state which has been rotated about 90° by the Faraday rotators in the rotating mode and (ii) an optical data signal which has been reflected from the target and has a polarization state which has been rotated about 0° by the Faraday rotators in the non-rotating mode such that optical interference between the optical reference signal and the optical data signals which have been reflected from the target is controlled by selection of the polarization rotating mode or the non-rotating mode of the probe; and
(f) a probe signal input/output for providing the source optical signal to the target and collecting optical data signals which have been reflected from the target.

15. The in-line optical probe according to claim 14, wherein the first Faraday rotator is provided with a fixed magnet.

16. The in-line optical probe according to claim 14, wherein the second Faraday rotator is provided with a magnetic coil.

17. The in-line optical probe according to claim 15, wherein the second Faraday rotator is switchable between the rotating mode and the non-rotating mode by application of current to a magnetic coil.

18. The in-line optical probe according to claim 14, further comprising a second lens disposed in-line with the single mode input/output fiber, the first lens, the reference reflector, the first and second Faraday rotators and the probe input/output.

19. The in-line optical probe according to claim 14, wherein a second lens is provided, and said second lens is adapted to focus the optical input signal toward the probe signal input/output and to capture optical data signals which have been reflected from the target.

20. The in-line optical probe according to claim 19, wherein the first and second lenses and the first and second Faraday rotators are located at a central portion of the probe and the central portion of the probe has a maximum diameter span of less than 30 MM.

21. The in-line optical probe according to claim 19, wherein the central portion of the probe has a maximum cross-section span of less than 20 mm.

22. The in-line optical probe according to claim 20, wherein the central portion of the probe has a maximum cross-section span of from about 5 mm to about 10 mm.

23. An optical probe suitable for medical or dental tomography comprising:
(a) an optical fiber suitable for connecting the probe to an optical signal source and an optical data analyzer;
(b) at least a first lens;
(c) a reference reflector;
wherein:
(i) the optical fiber is adapted for providing an optical source signal to the first lens and receiving an optical reference signal as well as receiving reflected optical data signals which are derived from the optical source signal and reflected from a target;
(ii) the first lens is adapted to focus the reference signal and reflected optical data signals into the optical fiber and adapted for collimating the optical source signal along an axis of the probe; and
(iii) the reference reflector is adapted to generate the reference signal from the optical source signal by reflecting a portion of the optical source signal;
(d) a first Faraday rotator, the first Faraday rotator being operative to rotate the polarization state of optical signals in a first direction of rotation by about 22.5° in a single pass;
(e) a second Faraday rotator, the second Faraday rotator being operative to rotate the polarization state of traversing optical signals by about +22.5° in a single pass with respect to the first direction of rotation in a rotating mode and being further operative in a non-rotating mode to rotate the polarization of traversing optical signals by about −22.5° in a single pass with respect to the first direction of rotation;
whereby the optical probe is configured to provide the optical fiber with the optical reference signal generated from the optical source signal as well as provide (i) an optical data signal which has been reflected from the target and has a polarization state which has been rotated about 90° by the Faraday rotators in the rotating mode or and (ii) an optical data signal which has been reflected from the target and has a polarization state which has been rotated about 0° by the Faraday rotators in the non-rotating mode such that optical interference between the optical reference signal and the optical data signals which have been reflected from the target is controlled by selection of the rotating mode or the non-rotating mode of the probe; and
(f) a probe signal input/output for providing the source optical signal to the target and collecting optical data signals which have been reflected from the target.

24. The optical probe according to claim 23, wherein the first Faraday rotator is provided with a fixed magnet.

25. The optical probe according to claim 24, wherein the second Faraday rotator is provided with a magnetic coil.

26. The optical probe according to claim 23 further comprising a second lens.

27. In a method of performing medical or dental tomography including generally reflecting a broadband optical source signal from a target area and analyzing the reflected optical signal, the improvement comprising:

(a) providing a broadband optical signal to an optical probe comprising: (i) an optical fiber suitable for connecting the probe to an optical signal source and an optical data analyzer; (ii) at least a first lens; (iii) a reference reflector; wherein: (A) the optical fiber is adapted for providing the optical source signal to the first lens and receiving an optical reference signal as well as receiving reflected optical data signals which are derived from the optical source signal and reflected from a target; (B) the first lens is adapted to focus the reference signal and reflected optical data signals into the optical fiber and adapted for collimating the optical source signal along an axis of the probe; and (C) the reference reflector is adapted to generate the reference signal from the optical source signal by reflecting a portion of the optical source signal; (iv) a first Faraday rotator, the first Faraday rotator being operative to rotate the polarization state of traversing optical signal in a first direction of rotation by about 22.5° in a single pass; (v) a second Faraday rotator, the second Faraday rotator being operative to rotate the polarization state of traversing optical signals by about +22.5° in a single pass with respect to the first direction of rotation in a rotating mode and being further operative in a non-rotating mode to rotate the polarization state of traversing optical signals by about −22.5° in a single pass with respect to the first direction of rotation; whereby the optical probe is configured to provide the optical fiber with the optical reference signal generated from the optical source signal as well as provide (A) an optical data signal which has been reflected from the target and has a polarization state which has been rotated about 90° by the Faraday rotators in the rotating mode and (B) an optical data signal which has been reflected from the target and has a polarization state which has been rotated about 0° by the Faraday rotators in the non-rotating mode such that optical interference between the optical reference signal and the optical data signals which have been reflected from the target is controlled by selection of the rotating mode or the non-rotating mode of the probe; and (vi) a probe signal input/output for providing the source optical signal to the target and collecting optical data signals which have been reflected from the target;

(b) generating a reference signal in the probe from the source signal and generating a first optical data signal which has been reflected from a target and has a polarization which has been rotated about 90° by the Faraday rotators and generating a second optical data signal which has been reflected from a target and has a polarization which has been rotated about 0° by the Faraday rotators; and (c) analyzing the reference signal and the first and second optical data signals.

* * * * *